United States Patent [19]

Carobbi et al.

[11] Patent Number: 4,536,221
[45] Date of Patent: Aug. 20, 1985

[54] PROCESS FOR PREPARING LACTULOSE FROM LACTOSE, IN THE FORM OF A SYRUP OR A CRYSTALLINE PRODUCT

[75] Inventors: Renato Carobbi, Pistoia; Sandro Miletti, Florence; Vittorio Franci, San Piero a Sieve, all of Italy

[73] Assignee: SIRAC Spa, Milan, Italy

[21] Appl. No.: 518,846

[22] Filed: Aug. 1, 1983

[30] Foreign Application Priority Data

Dec. 17, 1982 [IT] Italy ................ 24814 A/82

[51] Int. Cl.$^3$ ................ C13K 5/00
[52] U.S. Cl. ................ 127/30; 127/46.2; 536/125; 536/127
[58] Field of Search ........ 127/30, 31, 42, 46.1, 127/46.2, 46.3, 61; 536/1.1, 125, 127

[56] References Cited

U.S. PATENT DOCUMENTS

| | | | |
|---|---|---|---|
| 3,505,309 | 4/1970 | Carubelli | 536/125 |
| 3,514,327 | 5/1970 | Parrish | 127/42 |
| 3,546,206 | 12/1970 | Guth et al. | 127/42 |
| 3,716,408 | 2/1973 | Nagasawa et al. | 127/46.1 |
| 3,816,174 | 6/1974 | Nagasawa et al. | 127/46.1 |
| 4,067,748 | 1/1978 | Rowe | 127/31 |
| 4,069,104 | 1/1978 | Barker et al. | 536/125 |
| 4,142,916 | 3/1979 | Ogasa et al. | 127/30 |
| 4,160,675 | 7/1979 | Pannekeet et al. | 127/46.2 |
| 4,273,922 | 6/1981 | Hicks | 127/46.1 |
| 4,394,178 | 7/1983 | Chao et al. | 127/46.3 |

FOREIGN PATENT DOCUMENTS 47-39545 12/1972 Japan.
1232554 5/1971 United Kingdom.

*Primary Examiner*—Ivars Cintins
*Attorney, Agent, or Firm*—Stevens, Davis, Miller & Mosher

[57] ABSTRACT

A process for preparing lactulose from lactose, in the form of a concentrated syrup or high purity crystals, for pharmaceutical use or for use as a sweetener.

The process is characterized by using as the lactose epimerizing agent a mixture of equal parts of MgO and sodium hydrosulphite, each component being used to the extent of between 0.05 and 0.2% by weight with respect to the lactulose, at a temperature of about 100° C. The epimerization is complete in a few minutes.

The crystalline lactulose is obtained by crystallization from ethanol.

8 Claims, No Drawings

PROCESS FOR PREPARING LACTULOSE FROM LACTOSE, IN THE FORM OF A SYRUP OR A CRYSTALLINE PRODUCT

This invention relates to a new process for preparing lactulose from lactose, in the form of a syrup or a pure crystalline product.

Lactulose or 4-O-β-D-galactopyranosyl-D-fructose is known to be a synthetic disaccharide which is currently used in the form of syrup in the treatment of intestinal affections, or in the form of a crystalline product as a sweetner replacing saccharose.

Many processes are also known for preparing lactulose by the epimerisation of lactose, which is a widely available natural disaccharide of formula 4-O-β-D-galactopyranosyl-D-glucose.

Some of these processes are based essentially on the epimerisation of lactose by strong alkalis such as Ca(OH)$_2$, NaOH, KOH and strong organic bases.

These processes have the drawback of leading to the formation of large percentages of by-products which are difficult to separate and are coloured, and which not only strongly decrease the lactulose yield but also make it difficult both to use the lactulose syrup as such, and to prepare it as a crystalline product.

A further group of processes uses sodium tetraborate or sodium aluminate as the epimerising agent.

Although these processes lead to a higher lactulose yield and a more pure product, they are industrially unsatisfactory both because of the difficulty of filtering off the aluminium hydrate and because of the difficulty of quantitatively removing the boric acid.

Finally, processes which use strongly alkaline ion exchange resins for the epimerisation are too costly, and do not allow lactulose to be produced at market prices.

A lactulose production process has also been proposed in which lactulose is treated with a basic Mg derivative in an inert gaseous atmosphere (Spanish patent No. 397,810).

This process has never been used in practice because it utilises initial lactose solutions which are relatively dilute and is extremely slow, requiring between 10 and 20 hours for the completion of epimerisation. Both these factors make the process insignificant from an industrial viewpoint.

We have now discovered the subject matter of the present invention, namely that it is possible to obtain lactulose on an industrial scale with high yields and high purity by epimerising lactose with a mixture of equal parts of a basic magnesium salt and sodium hydrosulphite at a temperature of 90°–100° C.

The basic Mg salt can be the oxide, hydroxide or carbonate, and preferably MgO.

The reaction is conducted in the homogeneous phase using an aqueous lactose solution at a concentration of between 60 and 70%, and adding to the solution sodium hydrosulphite and magnesium oxide to the extent of between 0.05 and 0.2% by weight for each of said components with respect to the lactose.

The solution obtained is heated to 100° C. and then cooled. The reaction is generally complete in ten minutes.

The lactose which separates out on cooling the aqueous solution is separated by filtration, and the solution is then passed through a column of strong cationic resin and a column of weak anionic resin in order to remove the Mg and Na ions and the relative anions.

The purified solution is concentrated under vacuum at 60° C. until a density of 1.4 at the concentration temperature is obtained.

Further lactose crystallises on cooling the aqueous concentrate, and is separated by filtration or centrifuging.

The syrup composition at this stage is on average the following:
- lactulose: 50% by weight
- galactose: 4–5% by weight
- lactose: 4–5% by weight
- other sugars: 1–2% by weight The yield at this stage is 35–40% of lactulose with respect to the initial lactose.

The syrup is absolutely free from coloration and can be used as such for all normal pharmaceutical uses.

If lactulose is required in the crystalline state, the syrup can be further processed as follows.

The syrup is further concentrated to obtain a spongy mass with 5–10% of residual moisture, after which ethanol is added in the proportion of about 1:15 with respect to the solid residue, and the mixture heated under reflux until the mass has dissolved. The ethanol used must not contain more than 5% of H$_2$O.

On cooling to a temperature of around 15°–20° C., the syrup stratifies into a solid mass which decants and into an overlying alcoholic solution.

The solid mass, which contains essentially all the lactose and the other sugars together with part of the lactulose, is separated and recycled.

On concentrating the clear solution at ordinary pressure, possibly after seeding, crystalline lactulose is separated with the following average composition:
- lactulose: 98–99%
- other sugars: 1–2%

Crystalline lactulose at such a high purity has not been obtained with any of the industrial processes carried out up to the present time.

The crystalline lactulose yield is 35–40% with respect to that contained in the starting syrup, which had approximately 50% of lactulose.

Thus on an overall basis, taking account of the recycled quantities, the effective loss of lactulose does not exceed 3–5%.

The ethanol is also recovered by distillation, with a loss not exceeding 5–10%. It is recycled after making-up the missing quantity.

A practical example is described hereinafter in order to clarify the operational details of the process according to the present invention, but it must in no way be considered as limitative of the inventive concept of the present invention.

The scope of the invention covers all those embodiments and equivalent means which are apparent to an expert of the art.

EXAMPLE 0.750 kg of lactose, 0.750 g of sodium hydrosulphite and 0.400 kg of deionised water are fed into a two liter flask fitted with an agitator. The lactose is dissolved by heating to 95° C., and 0.750 g of magnesium oxide are added.

The reaction mixture is heated to 100° C. and kept at this temperature for 10 minutes.

It is cooled, and unreacted lactose is filtered off and re-used for a second preparation.

The clear solution is passed firstly through a column of strong cationic resin and then through a column of weak anionic resin.

The solution is concentrated under vacuum to a density of about 1.4 at 60° C., is cooled firstly with running water and then with brine to 5° C., and the additional lactose which precipitates is filtered off.

In this manner 0.530 kg of a clear solution of pH between 4 and 6 is obtained, having the following weight composition:

Lactulose: 50%
  Galactose: 4.3%
  Lactose: 4.5%
  Other sugars: 2%

Yield approximately 35% with respect to the initial lactose.

This syrup can be used as such.

The solution was analysed by HPLC under the following experimental conditions:

Column: $\phi$4 mm. 1=250 mm
  Filling: Lichrosorb $NH_2$ (10 microns)
  Column temperature: 40°±0.5° C.
  Detector: UV spectrophotometer—reading at 192 nm
  Mobile phase: 20% aqueous solution of 0.01M monobasic potassium phosphate and 80% of acetonitrile
  Flow: 2.5 ml/minute
  Quantity injected: 20 $\mu$l of a solution having an approximate concentration of 10% total sugars 0.5 kg of 50% lactulose syrup obtained in the previous stage is fed into a 5 liter flask, and dried under a vacuum of 1–5 Torr until a white spongy mass is obtained with a residual moisture content of less than 7%.

4.5 liters of 96% ethanol are added, and the mixture heated under reflux until a clear solution is obtained.

It is cooled to 15°–20° C. until a viscous mass forms and deposits on the container base, after which the overlying alcoholic solution is decanted and the clear solution concentrated at ordinary pressure after adding lactulose seed crystals.

When 2.5 liters of alcohol have distilled off, heating is stopped and agitation is continued, allowing the temperature to fall to 40°–45° C.

The crystallised lactulose is filtered off, washed with ethanol and dried under vacuum at 60°–80° C.

Yield 0.100 kg of crystalline product of the following composition:

lactulose 98.5%
  other sugars 1.5%

Yield approximately 40% with respect to the lactulose contained in the syrup.

This crystalline lactulose can be used as a sweetener.

Both the residue from the first alcohol extraction and the sugars contained in the ethanolic mother liquor from the final lactulose crystallisation were taken up in water and re-used for further processing.

The total lactulose loss was about 3%.

The ethyl alcohol was also recovered both during the solution concentration and during the drying of the lactulose crystals.

The alcohol loss was 7%, and was made-up by adding alcohol.

We claim:

1. A process for preparing lactulose from lactose, comprising adding to an aqueous solution containing 60%–70% of lactose, a basic magnesium compound and sodium hydrosulphite in amounts corresponding to 0.05%–0.2% by weight of each of the added compounds with respect to the lactose and heating the solution to a temperature of from 90° C. to 100° C. to effect isomerization of the lactose to lactulose in the presence of the magnesium compound and the sodium hydrosulfite to produce a reaction solution containing the lactulose.

2. A process as claimed in claim 1, wherein the Mg compound is MgO.

3. A process as claimed in claim 1, wherein the reaction solution containing the lactulose is purified by successive passages through a cationic exchange resin and an anionic exchange resin, and is then concentrated to a density of 1.4.

4. A process as claimed in claim 1, wherein the solution is evaporated until a spongy mass containing 5–10% of moisture is obtained, the lactulose being extracted from this mass by hot ethanol, from which it is crystallised.

5. A process as claimed in claim 4, wherein the ethanol contains a maximum of 5% of water.

6. A process as claimed in claim 4, wherein the ethanol is added in the proportion of 1:15 with respect to the spongy mass, and the mixture is heated under reflux until complete solubilisation is obtained.

7. A process as claimed in claim 4, wherein the ethanolic solution containing the lactulose is cooled to about 15°–20° C.

8. A process as claimed in claim 7, wherein the crystalline lactulose is obtained by concentration in the presence of lactulose seed crystals.

* * * * *